United States Patent [19]

Jungblut et al.

[11] Patent Number: 5,124,321

[45] Date of Patent: Jun. 23, 1992

[54] 17-HALOMETHYLENE ESTRATRIENES

[75] Inventors: Peter Jungblut, Neustadt-Bueren; Rudolf Wiechert; Rolf Bohlmann, both of Berlin, all of Fed. Rep. of Germany

[73] Assignee: Schering Aktiengesellschaft, Berlin & Bergkamen, Fed. Rep. of Germany

[21] Appl. No.: 280,912

[22] Filed: Dec. 7, 1988

[30] Foreign Application Priority Data

Dec. 7, 1987 [DE] Fed. Rep. of Germany ....... 3741800

[51] Int. Cl.⁵ .................. C61K 31/56; C07J 13/00
[52] U.S. Cl. ................... 514/182; 514/117; 514/176; 540/113; 552/530
[58] Field of Search ...... 260/397.5; 514/182, 514/176, 117; 552/530; 540/113

[56] References Cited

U.S. PATENT DOCUMENTS 4,011,314 3/1977 Petzoldt et al. ............... 514/182

OTHER PUBLICATIONS

PDR, 45th Edition, 1991, pp. 1070-1073.
The Merck Index, Tenth Edition, 1983, p. 8921.
Bestmann, Old and New Ylid Chemistry, Pure & App. Chem., vol. 52, pp. 771-788, Pergamon Press Ltd., 1980.
Huggins et al., "Induction and Extinction of Mammary Cancer", Science, Jul. 27, 1962, vol. 137, No. 3526, pp. 257-262.
Burton et al., "A Practical Synthesis of Fluoromethyl-triphenylphosphonium Salts," Journal of Fluorine Chemistry, 27 (1985) 85-89.
Hofle et al., "4-Dialkylaminopyridine als hochwirksame Acylierungskatalysatoren", Neue synthetische Methoden (25), pp. 602-615.
B. Runnebaum et al., Female Contraception: Update and Trends, Springer-Verlag, Berlin, 1988, pp. 64-90, 109-121, 122-128, and 129-140.
CA:111, 214810y (1989) Preparation . . . by Jungblut Peter et al.

Primary Examiner—Mukund J. Shah
Assistant Examiner—Jyothsna Venkat
Attorney, Agent, or Firm—Millen, White & Zelano

[57] ABSTRACT

17-halomethylene estratrienes of Formula I

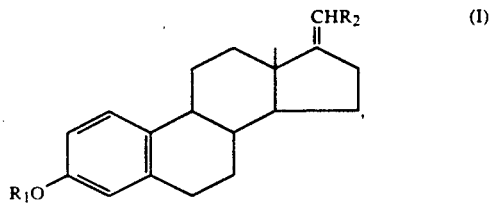

wherein
$R_1$ is hydrogen, a methyl or acyl group, and
$R_2$ is a halogen atom, show low affinity to the estrogen receptor and bring about a cellular membrane and blood/lymphatic vessel permeability that is increased as compared with estradiol.

16 Claims, No Drawings

17-HALOMETHYLENE ESTRATRIENES

SUMMARY OF THE INVENTION

The invention relates to 17-halomethylene estratrienes, processes for their production, pharmaceutical preparations containing these compounds, methods of treating estrogen deficiency symptoms and hormone-dependent tumors, and methods of contraception.

17-halomethylene estratrienes are characterized by Formula I

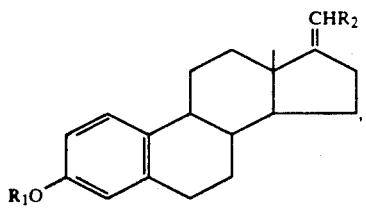

wherein $R_1$ is a hydrogen atom, a methyl or acyl group, and $R_2$ is a halogen atom.

Suitable acyl groups are physiologically compatible groups derived from acids customarily used for the esterification of hydroxy steroids. The identity and structure of the acyl moiety are not critical. Suitable acyl groups include organic carboxylic acids of 1-12 carbon atoms, e.g., hydrocarbon acids, pertaining to the aliphatic, cycloaliphatic, aromatic or aromatic-aliphatic series which can be saturated or unsaturated, mono- or poly-basic and/or substituted. Examples that can be mentioned for the substituents are alkyl (e.g., of 1-4 C atoms), hydroxy, alkoxy (e.g., of 1-4 C atoms), oxo or amino groups (e.g., amino and mono- or dialkylamino (1-4 C-alkyl groups)) and halogen atoms. Among these are also the usual inorganic acids.

Examples of such carboxylic acids of 1-12 carbon atoms include alkanoyl groups from formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, trimethylacetic acid, tertbutylacetic acid, cyclopentylacetic acid, diethylaminoacetic acid, lactic acid, succinic acid, adipic acid; other preferred groups include benzoic acid, nicotinic acid, morpholinoacetic acid, etc.

Examples of inorganic acids include sulfuric and phosphoric acids.

The esters of succinic acid, adipic acid, sulfuric acid, and phosphoric acid can optionally be converted with an alkali into the water-soluble salts.

Hetero acyl groups can be derived from heterocyclic acids comprising 1-2 fused rings, wherein each ring contains 4-7 ring atoms and 1-2 hetero atoms, the hetero atoms comprising O, N and/or S. Suitable acyl groups include that from pyrrolidino-, piperidino-, piperazino-, morpholinosulfonic acid, etc.

Suitable halogen atoms throughout the foregoing are fluorine, chlorine, bromine and iodine, preferably fluorine and chlorine.

It has been found that the estratrienes substituted by halomethylene in the 17-position differ markedly from the estrones. As compared with the estrones, from which they are produced, the compounds of general Formula I show a lower affinity to the estrogen receptors than estradiol and, as compared with estradiol, bring about increased cellular membrane and blood/lymphatic vessel permeability.

In the estrogen receptor binding test for estrogenic activity with the use of cytosol from pig uterus homogenate and of 6,7$^3$H estradiol as the reference compound, the compounds of Formula I show a lower affinity for the estrogen receptor.

The following table indicates the competition at the receptor in percent.

TABLE

| | Estrogen Receptor Binding Test | |
|---|---|---|
| Compound | Mol | % Competition |
| Estradiol | $2 \times 10^{-8}$ | 49 |
| | $2 \times 10^{-7}$ | 88 |
| | $2 \times 10^{-6}$ | 96 |
| 17-Fluoro-methylene-1,3,5(10)-estratrien-3-ol | $2 \times 10^{-8}$ | 12 |
| | $2 \times 10^{-7}$ | 23 |
| | $2 \times 10^{-6}$ | 78 |

In a uterus growth test with immature, 23-day-old Sprague-Dawley rats, for example, 17-fluoromethylene-1,3,5(10)-estratrien-3-ol exhibits 1/40 of the uterotropic activity of estradiol, based on moist uterus weights including intrauterine fluid. When DNA content is employed as a measure of the uterus cell number, then approximately 1/70 of estradiol activity is found for 17-fluoromethylene-1,3,5(10)-estratriene.

For performing the test, the immature female rats receive once daily over 3 days estradiol or 17-fluoromethylene-1,3,5(10)-estratrien-3-ol subcutaneously. On the 4th day, the animals are sacrificed, and the uterus weight or the DNA content per uterus is determined.

A uterus weight of 67 mg is obtained with 0.1 ug of estradiol or with 4.2 ug of 17-fluoromethylene-1,3,5(10)-estratrien-3-ol. A DNA content of 381 ug is the result with 0.1 ug of estradiol or with 7.3 ug of 17-fluoromethylene-1,3,5(10)-estratrien-3-ol.

Upon local administration of estradiol or 17-fluoromethylene-1,3,5(10)-estratrien-3-ol into the uterine lumen of a pig, a uterine edema is produced which is more strongly pronounced in case of the 17-fluoromethylene compound than in case of estradiol. The extent of edema can be determined by ascertaining the albumin and DNA content of the uterus.

Intrauterine injection of $1 \times 10^{-6}$-molar solutions (20-50 ml/uterus) of the compounds to be tested leads, after 120 minutes, in case of estradiol, to an increase in the albumin content of about 17 mg of albumin/1 mg of DNA and, in case of the corresponding 17-fluoromethylene compound, to an increase of 36 mg albumin/1 mg DNA.

Introduction of the test compound into a uterine horn of a female pig brings about edema formation only at that location; the untreated horn is not affected. The compound is bound to the receptor without subsequent renewed synthesis of receptor.

Accordingly, the finding for the compounds of Formula I is an activity disproportionation indicating a lower activity in the cell nucleus by way of the estrogen receptor, with an edema formation that is unchanged as compared with estradiol.

The compounds of Formula I are substrates for intracellular enzymes, the products of which lead to an increase in cellular membrane and blood/lymphatic vessel permeability, which can be demonstrated as socalled "water imbibition" in the form of a massive edema in the target organ, the uterus. These compounds are especially suitable for the treatment of climacteric complaints, as well as generally for the treatment of symptoms occurring due to defunctionalization of the second activity segment of estradiol.

The active compounds are preferably administered orally, e.g. to mammals including humans, but they can also be administered locally and parenterally. For this purpose, the active compounds are processed according to conventional methods for the customary forms of administration together with the additives, excipients and/or solubilizers customary in galenic pharmacy. For the preferred oral administration, especially suitable are tablets, dragees, capsules, pills, aqueous suspensions or alcoholic solutions, and for local and parenteral administration, especially ointments and, respectively, oily solutions, such as, for example, sesame oil or castor oil solutions which can additionally contain, if desired, a solubilizer, e.g., benzyl benzoate.

The concentration of active compound in the pharmaceutical preparations depends on the type of administration and the field of usage. Thus, for example, tablets, dragees, capsules or pills can contain 10–150 μg of active compound per dosage unit, and oily solutions or ointments can contain 1–20 μg of active compound per milliliter.

In a preferred embodiment, the oral form of administration contains 10–100 μg of active agent.

After treating therapeutically castrated women, as well as women in the climacteric, all of whom suffered from hot flashes and moodiness with daily 10–100 μg of active compound according to Formula I, a marked decrease in discomfort occurred as early as after 2 days.

The systemic administration of compounds of Formula I to Sprague-Daley rats with mammary tumors induced by 7,12-dimethylbenzanthracene leads to cessation of tumor growth without any marked effect on the estrous cycle. The compounds are thus likewise suitable for the treatment of hormone-dependent tumors as compared to the known compound Tamoxifen. With the use of the compounds in daily amounts of 0.1–5 μg per kg, stimulation of growth of existing hormone-dependent tumors is prevented.

This antitumor activity can be demonstrated using any conventional protocol, e.g., as described in Science 137 (1962), 257–262.

The compounds of Formula I, being substances with a selective estrogenic activity, can also be utilized in preparations for contraception, preferably in combination with a progestationally active hormone component, e.g., levonorgestrel, gestodene, or desogestrel. Forms of administration that can be given orally contain preferably 10–100 μg of a compound of Formula I and 50–500 μg of a strongly effective gestagen per day. The compounds are administered analogously to the known compound Miorogynon(R).

17-halomethylene estratrienes of Formula I can be prepared according to this invention by reacting an estrone of Formula II

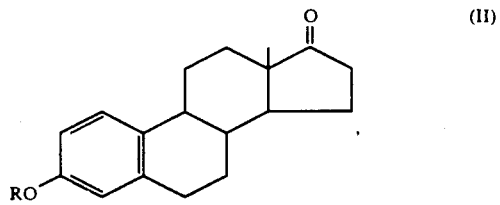

wherein R is a hydrogen atom or a methyl group, with a halomethylenylide, and optionally acylating a free hydroxy group.

The reaction with halomethylenylide takes place according to conventional methods, for example in an aprotic solvent, such as dimethyl sulfoxide, dimethylformamide, dioxane, tetrahydrofuran, or a mixture of these solvents at temperatures of between 20° and 40° C., a protective gas, such as nitrogen or argon being preferably employed during the reaction (Pure and Applied Chemistry 52 (1980) 771).

The halomethylenylide is suitably prepared in the reaction solution from halomethyltriphenylphosphonium salt with a base, such as sodium hydride, sodium hydroxide, potassium tert-butylate, sodium methylate or butyllithium (Journal Fluorine Chemistry 27 (1985) 85).

Especially suitable halomethyltriphenylphosphonium salts are fluoromethyltriphenylphosphonium tetrafluoroborate and chloromethyltriphenylphosphonium chloride.

The subsequent optional acylation takes place according to conventional methods for esterification of phenolic hydroxy groups, preferably with pyridine/acid anhydride or pyridine/acid chloride, at room temperature (Ang. Chemie 90 (1978) 602).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application, West German P. 37 41 800.9, filed Dec. 7, 1987, are hereby incorporated by reference.

EXAMPLES

Example 1

17.2 g of fluoromethyltriphenylphosphonium tetrafluoroborate [J. Fluorine Chem. 27: 85–89 (1985)] is suspended in 150 ml of dioxane and combined at 20° C. with 6.7 g of potassium tert-butylate in incremental portions, and further agitated for 0.5 hour. To this solution is added 2.0 g of 1,3,5(10)-estratrien-3-ol-17one in 30 ml of dioxane, and the mixture is stirred for 30 minutes. For working-up purposes, the mixture is poured on water, dried over sodium sulfate, and concentrated to dryness under vacuum. After purification by chromatography on silica gel with hexane/ethyl acetate, 1.63 g of 17-fluoromethylene-1,3,5(10)-estratrien-3-ol is obtained as an E/Z mixture, mp 125°–129° C. $[\alpha]_D + 68.1°$ (chloroform).

Example 2

17.2 g of chloromethyltriphenylphosphonium chloride is suspended in 150 ml of dioxane and combined at 20° C. with 6.7 g of potassium tert-butylate in incremental portions, and further stirred for 0.5 hour. To this solution is added 2 g of 3-[(tetrahydropyran-2-yl)oxy]-1,3,5(10)-estratrien-17-one in 30 ml of dioxane, and the mixture is stirred for 30 minutes. For working-up purposes, the mixture is poured on water, dried over sodium sulfate, and concentrated to dryness under vacuum, thus obtaining 17-chloromethylene-3-[(tetrahydropyran-2-yl)oxy]-1,3,5(10)-estratriene which, as a crude product, is dissolved in 50 ml of methanol and heated under reflux for one hour with 2 g of oxalic acid. Then the product is precipitated with ice water/sodium chloride taken up in ethyl acetate, dried over sodium sulfate, and concentrated to dryness under vacuum. After purification by chromatography on silica gel with hexane/ethyl acetate, 1.74 g of 17-chloromethylene-1,3,5(10)-estratrien-3-ol is obtained as an E/Z mixture having a melting point of 130°–133° C. $[\alpha]_D + 52.8°$ (chloroform).

Example 3

Analogously to Example 1, 2.0 g of 3-methoxyestrone is reacted to 1.67 g of 17-fluoromethylene-3-methoxy-1,3,5(10)-estratriene as an oil.

Example 4

1.0 g of 17-fluoromethylene-1,3,5(10)-estratrien-3-ol in 10 ml of pyridine is agitated with 5 ml of acetic anhydride for 2 hours at 20° C. Then the mixture is precipitated with sulfuric acid ice water, taken up in dichloromethane, washed neutral with sodium bicarbonate solution, dried over magnesium sulfate, and freed of solvent under vacuum. After chromatography on silica gel with hexane/ethyl acetate, 955 mg of 3-acetoxy-17-fluoromethylene-1,3,5(10)-estratriene is obtained.

Example 5

Analogously to Example 4, 1.0 g of 17-fluoromethylene-1,3,5(10)-estratrien-3-ol is reacted with 5 ml of butyric acid anhydride to form 1.03 g of 3-butyryloxy-17-fluoromethylene-1,3,5(10)-estratriene.

Example 6

Analogously to Example 4, 1.0 g of 17-fluoromethylene-1,3,5(10)-estratrien-3-ol is reacted with 5 ml of undecylic acid anhydride to produce 1.06 g of 17-fluoromethylene-3-undecyloxy-1,3,5(10)-estratriene.

Example 7

Analogously to Example 2, 2.0 g of 3-methoxyestrone is reacted to 1.59 g of 17-chloromethylene-3-methoxy-1,3,5(10)-estratriene as an oil.

Example 8

1.0 g of 17-chloromethylene-1,3,5(10)-estratrien-3-ol in 10 ml of pyridine is stirred with 5 ml of acetic anhydride for 2 hours at 20° C. Then the product is precipitated with sulfuric acid ice water, taken up in dichloromethane, washed neutral with sodium bicarbonate solution, dried over magnesium sulfate, and freed of solvent under vacuum. After chromatography on silica gel with hexane/ethyl acetate, 955 mg of 3-acetoxy-17-chloromethylene-1,3,5(10)-estratriene is obtained.

Example 9

Analogously to Example 8, 1.0 g of 17-chloromethylene-1,3,5(10)-estratrien-3-ol is reacted with 5 ml of butyric acid anhydride to 1.03 g of 3-butyryloxy-17-chloromethylene-1,3,5(10)-estratriene.

Example 10

Analogously to Example 8, 1.0 g of 17-chloromethylene-1,3,5((10)-estratrien-3-ol is reacted with 5 ml of undecylic acid anhydride to 1.06 g of 17-chloromethylene-3-undecyloxy-1,3,5(10)-estratriene.

Example 11

| Composition of a Dragee | |
| --- | --- |
| 0.010 mg | 17-Fluoromethylene-1,3,5(10)-estratrien-3-ol |
| 46.490 mg | Lactose |
| 26.800 mg | Cornstarch |
| 3.000 mg | Poly(1-vinyl-2-pyrrolidone) average MW 25,000 |
| 3.700 mg | Talc |
| 80.000 mg | Total weight, supplemented to about 140 mg with the usual sugar mixture. |

Example 12

Composition of an Alcoholic Solution 1 mg of 17-chloromethylene-1,3,5(10)-estratrien-3-ol is dissolved in 10 ml of 46% strength ethyl alcohol.

Ten drops (0.5 ml) contain 50 μg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17-halomethylene estratriene of the formula

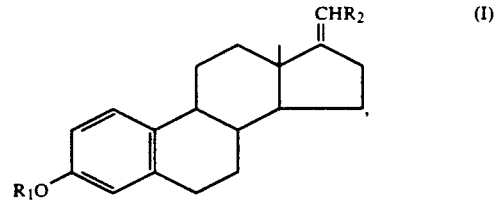

wherein
$R_1$ is hydrogen, methyl, or the acyl group of a $C_{1-12}$ hydrocarbon carboxylic acid said acyl groups being optionally substituted by $C_{1-4}$ alkyl, hydroxy, $C_{1-4}$-alkoxy, oxo, amino or halogen, or a mineral acid, and $R_2$ is halogen.

2. A compound of claim 1, wherein $R_1$ is $C_{1-12}$ alkanoyl.

3. A compound of claim 1, wherein $R_1$ is H.

4. A compound of claim 1, wherein $R_1$ is $CH_3$.

5. A compound of claim 1, wherein $R_2$ is fluorine.

6. A compound of claim 5, which is 17-fluoromethylene-1,3,5(10)-estratriene-3-ol, 17-fluoromethylene-3- methoxy-1,3,5(10)-estratriene, 3-butyryloxy-17-fluoromethylene-1,3,5(10)-estratriene, or 17-fluoromethylene-3-undecyloxy-1,3,5(10)-estratriene.

7. A compound of claim 1, wherein $R_2$ is chlorine.

8. A compound of claim 7, which is 17-chloromethylene-1,3,5(10)-estratriene-3-ol, 17-chloromethylene-3-methoxy-1,3,5(10)-estratriene, 3-acetoxy-17-chloromethylene-1,3,5(10)-estratriene, 3-butyryloxy-17-chloromethylene-1,3,5(10)-estratriene, or 17-chloromethylene-3-undecyloxy-1,3,5(10)-estratriene.

9. A compound of 1, wherein $R_1$ is H, $CH_3$ or $C_{1-12}$ alkanoyl.

10. A pharmaceutical preparation comprising an effective amount of a compound according to claim 1 and a pharmaceutically acceptable excipient.

11. A pharmaceutical preparation comprising an effective amount of a compound according to claim 6 and a pharmaceutically acceptable excipient.

12. A pharmaceutical preparation comprising an effective amount of a compound according to claim 8 and a pharmaceutically acceptable excipient.

13. A pharmaceutical preparation of claim 10, wherein said amount is 10–150 μg per dosage unit.

14. A method of treating estrogen deficiency symptoms, comprising administering to a patient in need of such treatment an effective amount of a compound of claim 1.

15. A method of preventing pregnancy, comprising administering to a female mammal contraceptively effective amount of a compound of claim 1.

16. A method of preventing pregnancy, comprising administering, in combination, to a female mammal contraceptively effective amounts of a compound of claim 1 and a progestationally active compound.

* * * * *